US009315898B2

(12) United States Patent
Suzuki et al.

(10) Patent No.: US 9,315,898 B2
(45) Date of Patent: Apr. 19, 2016

(54) TEM SAMPLE PREPARATION METHOD

(71) Applicant: HITACHI HIGH-TECH SCIENCE CORPORATION, Tokyo (JP)

(72) Inventors: Hidekazu Suzuki, Tokyo (JP); Ikuko Nakatani, Tokyo (JP)

(73) Assignee: HITACHI HIGH-TECH SCIENCE CORPORATION (JP)

( * ) Notice: Subject to any disclaimer, the term of this patent is extended or adjusted under 35 U.S.C. 154(b) by 485 days.

(21) Appl. No.: 13/761,332

(22) Filed: Feb. 7, 2013

(65) Prior Publication Data

US 2013/0209700 A1   Aug. 15, 2013

(30) Foreign Application Priority Data

Feb. 10, 2012   (JP) .................. 2012-027692

(51) Int. Cl.
| *B44C 1/22* | (2006.01) |
| *C23C 16/48* | (2006.01) |
| *G01N 1/28* | (2006.01) |
| *G01N 1/32* | (2006.01) |

(52) U.S. Cl.
CPC .............. *C23C 16/486* (2013.01); *G01N 1/28* (2013.01); *G01N 1/32* (2013.01); *H01J 2237/31745* (2013.01)

(58) Field of Classification Search
CPC ..... G01N 1/28; G01N 1/32; H01J 2237/3174; H01J 2237/31749; H01L 2224/2763
USPC ................................. 216/66, 67, 71
See application file for complete search history.

(56) References Cited

U.S. PATENT DOCUMENTS

| 5,656,811 | A | 8/1997 | Itoh et al. ...................... 250/309 |
| 5,798,529 | A * | 8/1998 | Wagner .................... 250/492.21 |
| 6,417,512 | B1 | 7/2002 | Suzuki |
| 2002/0074496 | A1 | 6/2002 | Sadayama ..................... 250/311 |
| 2004/0245464 | A1 * | 12/2004 | Iwasaki et al. ................ 250/307 |
| 2008/0078742 | A1 | 4/2008 | Hu et al. ........................ 216/57 |

FOREIGN PATENT DOCUMENTS

| CN | 1162190 | 10/1997 |
| CN | 101153833 | 4/2008 |
| EP | 0784211 | 7/1997 |
| JP | 7333120 | 12/1995 |
| JP | 2000035391 | 2/2000 |
| JP | 2001319954 | 11/2001 |
| JP | 2002174571 | 6/2002 |
| JP | 2011185845 | 9/2011 |

OTHER PUBLICATIONS

First Notification of Office Action issued Dec. 23, 2015 in Chinese Appln. No. 201310050889.X.

* cited by examiner

*Primary Examiner* — Binh X Tran
(74) *Attorney, Agent, or Firm* — Adams & Wilks

(57) ABSTRACT

A TEM sample preparation method including: placing a thin sample on a sample holder so that a first side surface of the thin sample which is closer to a desired observation target is opposed to a focused ion beam column; setting a processing region, which is to be subjected to etching processing by a focused ion beam so as to form a thin film portion including the observation target and having a thickness direction substantially parallel to a thickness direction of the thin sample, to a region of the first side surface that is adjacent to the thin film portion; and performing the etching processing to a portion of the thin sample extending from the first side surface thereof to a front surface thereof by irradiating the processing region with the focused ion beam from the focused ion beam column.

9 Claims, 5 Drawing Sheets

TEM SAMPLE PREPARATION METHOD

CROSS-REFERENCE TO RELATED APPLICATIONS

This application claims priority from Japanese Patent Application No. 2012-027692 filed on Feb. 10, 2012, the entire contents of which are incorporated herein by reference.

TECHNICAL FIELD

Aspects of the present invention relate to a method of preparing a TEM sample by etching processing using a focused ion beam.

BACKGROUND

In related-art, Transmission Electron Microscope (TEM) observation is known as a method of observing a micro region in a sample for analyzing defects in a semiconductor device or other purposes. In TEM observation, when preparing a sample for obtaining a transmission electron image, it is necessary to prepare a TEM sample having a thin film portion, which has such a thickness that allows an electron beam to transmit therethrough, at a portion thereof.

In recent years, as a method of preparing a TEM sample, a TEM sample preparation method using a focused ion beam has been used. In this method, a peripheral portion of a sample is subjected to etching processing so that a portion including a desired observation region inside the sample is left. Then, the remaining portion is subjected to etching processing until the remaining portion has such a thickness that allows an electron beam to transmit therethrough, to thereby form a thin film portion. In this manner, a TEM sample can be prepared with pinpoint accuracy with regard to the portion including the desired observation region.

However, there has been a problem in that, in preparing the TEM sample, if the thickness of the thin film portion becomes smaller, the thin film portion is curved due to internal stress. As a method for solving the problem, there has been proposed a technology of forming a slit in a curved portion so as to release the thin film portion from stress (see JP-A-2000-35391).

In recent years, sizes of the device structure and defects as observation targets have become smaller. Accordingly, in TEM observation, in order to observe only the observation target accurately, it is necessary to prepare a TEM sample having an extremely small thin film portion having a thickness of, for example, 50 nm or less. In this case, there has been a problem in that the thin film portion is bent and curved even when a slit is formed therein as in the above-mentioned related-art technology.

SUMMARY

The present invention provides a TEM sample preparation method capable of preparing a TEM sample in which a thin film portion is not curved when preparing a TEM sample having a thin film portion having a small thickness.

According to an aspect of the present invention, there is provided a TEM sample preparation method including: placing a thin sample on a sample holder so that a first side surface of the thin sample, which is closer to a desired observation target inside the thin sample than a second side surface of the thin sample is to the observation target, is opposed to a focused ion beam column; setting a processing region, which is to be subjected to etching processing by a focused ion beam so as to form a thin film portion including the observation target and having a thickness direction substantially parallel to a thickness direction of the thin sample, to a region of the first side surface that is adjacent to the thin film portion; and performing the etching processing to a portion of the thin sample extending from the first side surface thereof to a front surface thereof by irradiating the processing region with the focused ion beam from the focused ion beam column.

According to this method, the etching processing is performed from the first side surface of the thin sample that is closer to the observation target than the second side surface of the thin sample is to the observation target, and hence, a thin film portion can be prepared with a smaller etching amount as compared to the case of performing etching processing from the second side surface opposite to the first side surface. Therefore, the etching amount can be reduced, and hence the thin film portion can be supported strongly by a portion of the thin sample where the etching has not been performed. Thus, the thin film portion can be prevented from being curved.

According to another aspect of the present invention, there is provided a TEM sample preparation method including: placing a thin sample including an observation target therein on a sample holder so that a first side surface of the thin sample, which is closer to the desired observation target than a second side surface of the thin sample is to the observation target, is opposed to a focused ion beam column; setting a processing region, which is to be subjected to etching processing by a focused ion beam, to a region of the first side surface; and performing the etching processing to a portion of the thin sample extending from the first side surface thereof to a front surface thereof by irradiating the processing region with the focused ion beam from the focused ion beam column, thereby forming a thin film portion including the observation target and having a thickness direction substantially parallel to a thickness direction of the thin sample.

According to the TEM sample preparation methods of the aspects of the present invention, a TEM sample can be prepared without curving the thin film portion.

DETAILED DESCRIPTION

A TEM sample preparation method according to an exemplary embodiment of the present invention will be described hereinafter.

Figure 1:
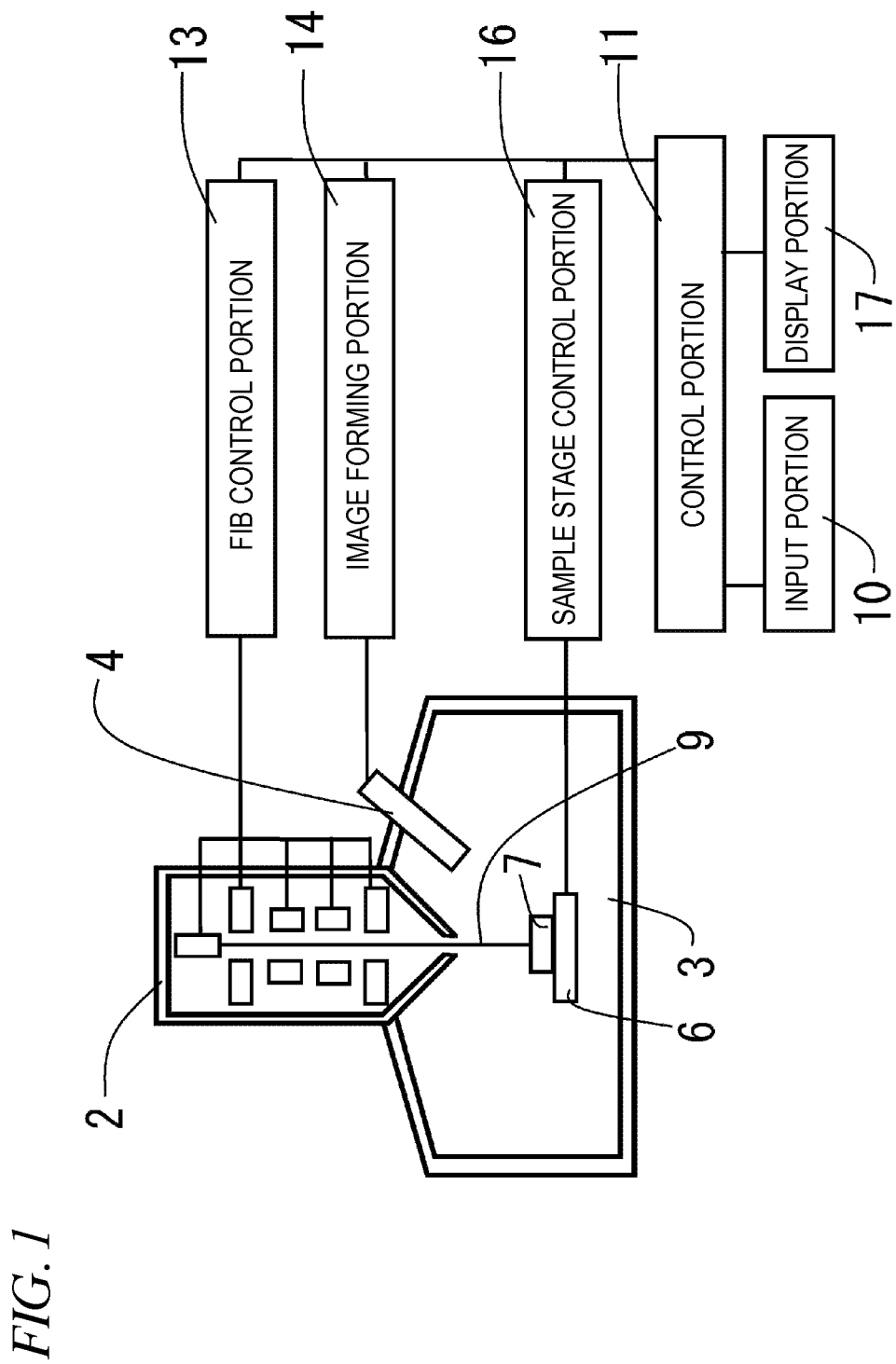
FIG. 1 is a configuration diagram of a focused ion beam apparatus according to an exemplary embodiment of the present invention.

As illustrated in FIG. 1, a focused ion beam apparatus for TEM sample preparation in the exemplary embodiment includes a FIB column 2 and a sample chamber 3. The FIB column 2 is capable of irradiating a sample 7 accommodated in the sample chamber 3 with an ion beam 9.

The focused ion beam apparatus further includes a secondary electron detector 4. The secondary electron detector 4 is capable of detecting secondary electrons generated from the sample 7 by irradiation of the ion beam 9.

The focused ion beam apparatus further includes a sample stage 6 for placing the sample 7 thereon. The sample stage 6 can be tilted to change an incident angle of the ion beam 9 to the sample 7. The movement of the sample stage 6 can be controlled by a sample stage control portion 16.

The focused ion beam apparatus further includes a FIB control portion 13, an image forming portion 14, and a display portion 17. The FIB control portion 13 controls the irradiation of the ion beam 9 from the FIB column 2. The image forming portion 14 forms a SIM image based on a signal for scanning the ion beam 9 sent from the FIB control portion 13 and a signal of the secondary electrons detected by the secondary electron detector 4. The display portion 17 is capable of displaying the SIM image.

The focused ion beam apparatus further includes an input portion 10 and a control portion 11. An operator inputs conditions on the apparatus control, such as an irradiation condition of the ion beam 9, to the input portion 10. The input portion 10 transmits the input information to the control portion 11. The control portion 11 transmits a control signal to the FIB control portion 13, the image forming portion 14, the sample stage control portion 16, or the display portion 17, to thereby control the operation of the apparatus.

The control of the apparatus will be described. For example, the operator sets an irradiation region of the ion beam 9 based on the SIM image displayed on the display portion 17. The operator inputs, via the input portion 10, a processing frame for setting the irradiation region on the observation image displayed on the display portion 17. When the operator inputs an instruction to start processing to the input portion 10, a signal indicating the irradiation region and a signal indicating the start of processing are transmitted from the control portion 11 to the FIB control portion 13, and the FIB control portion 13 radiates the ion beam 9 to the specified irradiation region of the sample 7. In this manner, the irradiation region input by the operator can be irradiated with the ion beam 9.

Figure 2A:
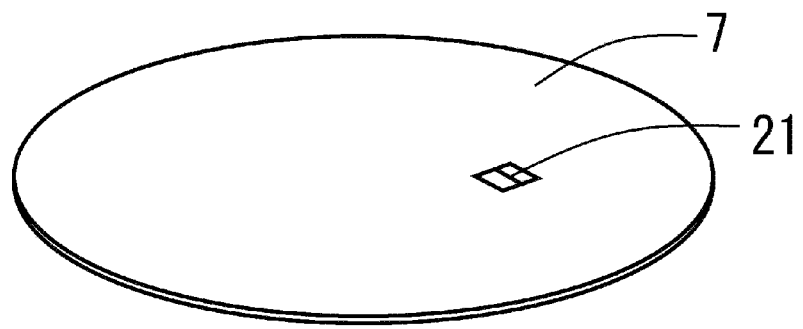
FIGS. 2A and 2B are explanatory diagrams of TEM sample preparation according to the exemplary embodiment of the present invention.
Figure 2B:
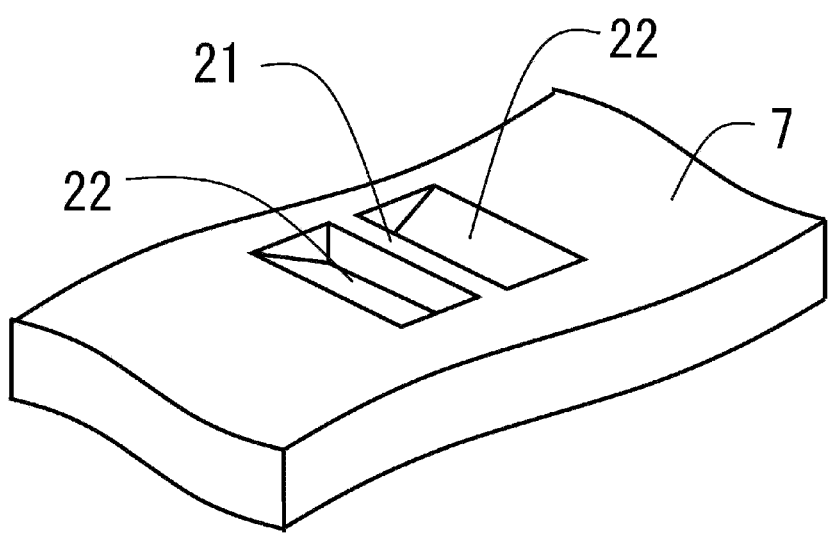

In the TEM sample preparation method according to the exemplary embodiment, as illustrated in FIG. 2A, a wafer-shaped sample 7 is partially processed by the ion beam 9, to thereby prepare a thin sample 21. FIG. 2B is an enlarged diagram of the thin sample 21 and its vicinity. The sample 7 is irradiated with the ion beam 9 to form a processing groove 22 while leaving the thin sample 21. In this stage, the thickness of the thin sample 21 is a thickness that does not allow an electron beam to transmit therethrough.

Figure 3A:
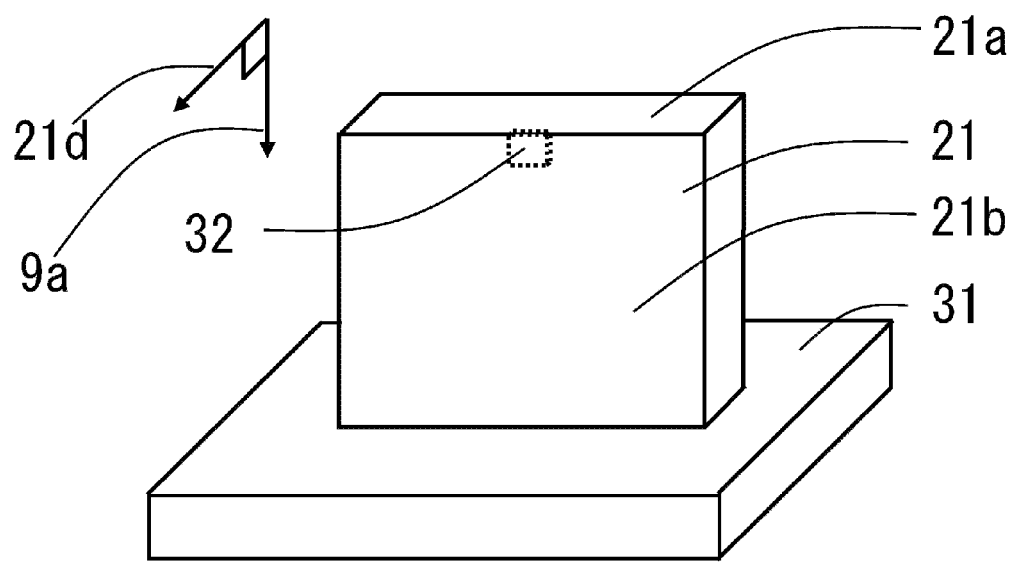
FIGS. 3A and 3B are explanatory diagrams of the TEM sample preparation according to the exemplary embodiment of the present invention.
Figure 5:
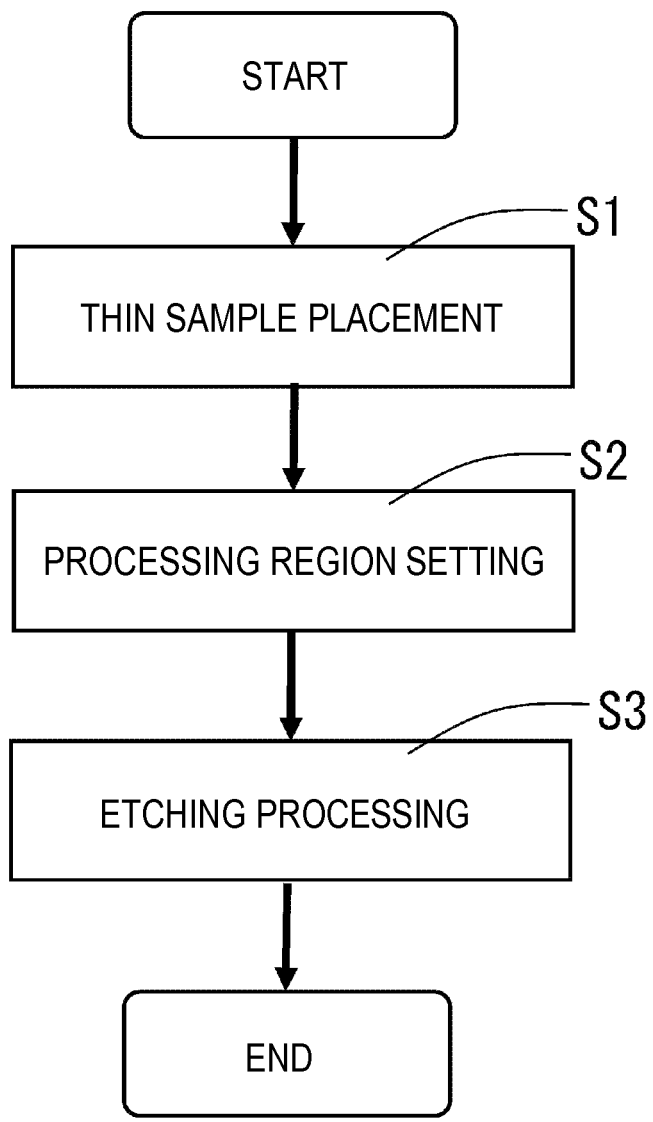
FIG. 5 is a flowchart of the TEM sample preparation according to the exemplary embodiment of the present invention.

Next, thin sample placement S1 in a flowchart of FIG. 5 is performed. The thin sample 21 is separated from the sample 7, and the thin sample 21 is placed on a sample holder 31 as illustrated in FIG. 3A. In this case, the thin sample 21 is placed on the sample holder 31 so that a desired observation target 32 may be located on the FIB column 2 side. In other words, the thin sample 21 is placed so that a side surface 21a thereof, which is closer to the observation target 32 than another side surface thereof is to the observation target 32, may be irradiated with the ion beam 9. The thin sample 21 is placed so that a thickness direction 21d of the thin sample 21 may be perpendicular to an irradiation direction 9a of the ion beam 9.

Next, processing region setting S2 for irradiation of the ion beam 9 is performed. In the processing region setting, a processing region is set on the SIM image displayed on the display portion 17, and an irradiation amount (dose amount) of the ion beam 9 is set.

Figure 3B:
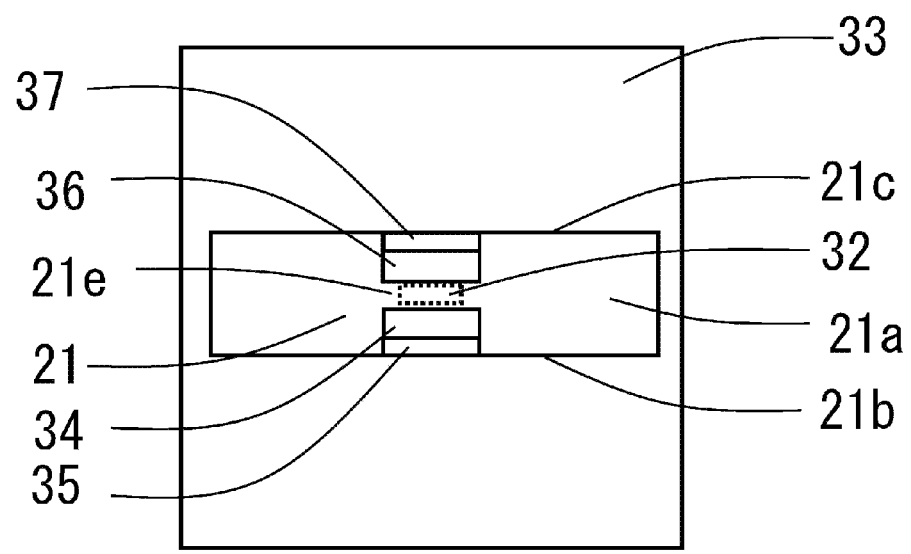

FIG. 3B is a SIM image 33 as viewed from the irradiation direction 9a of the ion beam 9. Processing regions 34, 35, 36, and 37 are set on the SIM image 33. The processing regions 34 and 36 are set so as to sandwich the observation target 32 on the side surface 21a. The longitudinal direction of the processing regions 34 and 36 is a direction perpendicular to the thickness direction of the thin sample 21. Then, the processing region 35 is set at a position that contacts with the processing region 34 and a front surface 21b, and the processing region 37 is set at a position that contacts with the processing region 36 and a rear surface 21c. The processing regions 34 and 36 constitute inner regions which sandwich therebetween the observation target 32, and the processing regions 35 and 37 constitute outer regions which extend from the front and rear surfaces 21b and 21c to the inner regions 34 and 36, respectively.

In this case, the longitudinal length of the processing regions 34 and 36 is set to a length necessary for observation of a TEM image of the observation target 32. This is because, if the longitudinal length of the processing regions 34 and 36 is unnecessarily large, the thin sample 21 is subjected to etching processing more than necessary, with the result that the strength for supporting a thin film portion 21e is weakened to curve the thin film portion 21e.

The processing regions 34, 35, 36, and 37 are set so that the thin film portion 21e having a thickness direction parallel to the thickness direction 21d of the thin sample 21 is left. In this manner, for observation of the TEM image of the observation target 32, the thin film portion 21e can be exposed without interrupting an optical path of the electron beam.

Then, the dose amount per unit area of the processing regions 34 and 36 through irradiation is set to be twice to ten times as large as the dose amount per unit area of the processing regions 35 and 37 through irradiation.

In general, the etching rate of a focused ion beam differs depending on the incident angle to the sample. The etching rate in the case where the focused ion beam enters the sample at an incident angle of about 0 degrees is twice as large as the etching rate in the case where the focused ion beam enters the sample at an incident angle of about 45 degrees, and is ten times as large as the etching rate in the case where the focused ion beam enters the sample at an incident angle of about 90 degrees.

In TEM sample preparation, etching processing is performed from the front surface 21b side of the processing region 35 or the rear surface 21c side of the processing region 37. In this case, the incident angle of the ion beam 9 to the thin sample 21 is almost 0 degrees. Then, in the course of advancing the processing from the front surface 21b side of the processing region 35 toward the processing region 34 side, the incident angle to the thin sample 21 changes in the range of 0 degrees to 45 degrees. This is because the incident angle of the ion beam 9 is determined by an angle with respect to a cross-section formed by the processing, and the angle of the cross-section changes during the processing.

In the processing regions 34 and 36, on the other hand, the incident angle of the ion beam 9 to the thin sample 21 is almost 90 degrees. Therefore, the incident angle of the ion beam 9 differs between the processing regions 34 and 36 and the processing regions 35 and 37, and hence the etching rate differs. The respective dose amounts are set as described above so that the etching amount is substantially uniform in the processing regions 34, 35, 36, and 37.

Figure 4:
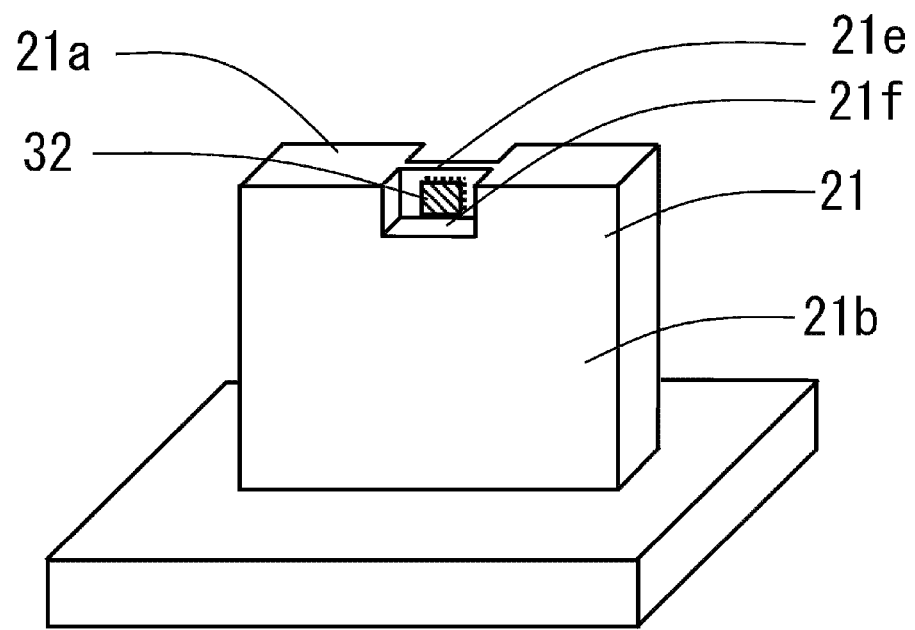
FIG. 4 is an explanatory diagram of the TEM sample preparation according to the exemplary embodiment of the present invention.

Next, etching processing S3 for irradiating the processing regions 34, 35, 36, and 37 with the ion beam 9 is performed. In this manner, a TEM sample having a shape as illustrated in FIG. 4 can be prepared.

Accordingly, the thin film portion 21e having the observation target 32 can be exposed. Only a portion including the observation target 32 is thinned, and hence the thin film portion 21e can be supported strongly by a portion of the thin sample 21 where the etching processing has not been performed. Thus, the thin film portion 21e is not curved even when the thickness of the thin film portion 21e is reduced.

Further, the dose amounts of the ion beam 9 to the processing regions 34, 35, 36, and 37 are controlled, and hence a bottom portion 21f formed by the etching processing becomes a surface substantially parallel to the side surface 21a. In this manner, even in the case of TEM observation by irradiating the thin film portion 21e with the electron beam from a direction parallel to the thickness direction 21d of the thin sample 21, it is possible to form such a shape that the optical path of the electron beam is not interrupted, and the etching amount of the thin sample 21 can be minimized.

In the exemplary embodiment, the thickness of the thin sample 21 is 10 μm and the thickness of the thin film portion 21e is 50 nm. Even in the case of a TEM sample having the thin film portion 21e with a small thickness, the etching processing amount of the thin sample 21 can be suppressed, and hence the TEM sample can be prepared without curving the thin film portion 21e.

The present invention provides illustrative, non-limiting aspects as follows:

(1) In a first aspect of the present invention, there is provided a TEM sample preparation method including: placing a thin sample on a sample holder so that a first side surface of the thin sample, which is closer to a desired observation target inside the thin sample than a second side surface of the thin sample is to the observation target, is opposed to a focused ion beam column; setting a processing region, which is to be subjected to etching processing by a focused ion beam so as to form a thin film portion including the observation target and having a thickness direction substantially parallel to a thickness direction of the thin sample, to a region of the first side surface that is adjacent to the thin film portion; and performing the etching processing to a portion of the thin sample extending from the first side surface thereof to a front surface thereof by irradiating the processing region with the focused ion beam from the focused ion beam column.

Accordingly, the etching processing is performed from the first side surface of the thin sample that is closer to the observation target than the second side surface of the thin sample is to the observation target, and hence, a thin film portion can be prepared with a smaller etching amount as compared to the case of performing etching processing from the second side surface opposite to the first side surface. Therefore, the etching amount can be reduced, and hence the thin film portion can be supported strongly by a portion of the thin sample where the etching has not been performed. Thus, the thin film portion can be prevented from being curved.

(2) In a second aspect of the present invention, there is provided a TEM sample preparation method according to the first aspect, wherein the processing region includes a first irradiation region at the front surface side thereof and a second irradiation region at the thin film portion side thereof, and wherein an irradiation amount of the focused ion beam is set to be larger in the second irradiation region than in the first irradiation region.

In general, the etching rate of a focused ion beam is larger in the case of processing a corner portion than in the case of processing a flat surface. Therefore, in the TEM sample preparation method, if the entire processing region is processed by the focused ion beam with the same irradiation amount, a portion that contacts with the front surface corresponds to a corner portion and this portion is etched greatly. In this case, the thin sample is subjected to etching processing more than necessary, with the result that the strength for supporting the thin film portion is lowered, and the thin film portion is curved. To deal with this problem, the irradiation amount of the portion that contacts with the front surface is set to be small. Thus, a thin film portion can be prepared without etching the thin sample more than necessary.

(3) In a third aspect of the present invention, there is provided a TEM sample preparation method according to the second aspect, wherein the irradiation amount of the focused ion beam in the second irradiation region is set to be twice to ten times as large as the irradiation amount of the focused ion beam in the first irradiation region.

(4) In a fourth aspect of the present invention, there is provided a TEM sample preparation method according to any one of the first to third aspects, wherein the etching processing includes forming a bottom surface which connects with the front surface and the thin film portion and is substantially parallel to the first side surface.

In TEM observation, the thin film portion is irradiated with an electron beam so that the electron beam transmits therethrough in a direction perpendicular to the thin film portion, that is, a thickness direction of the thin film portion. Accordingly, in the TEM sample preparation, etching processing is performed so that the thin film portion is exposed without interrupting an optical path of the electron beam. In this case, since the bottom surface which connects with the front surface and the thin film portion and is substantially parallel to the side surface is formed, the electron beam is not interrupted in the TEM observation, and further, the etching amount of the thin sample can be minimized. Thus, the thin film portion can be prevented from being curved.

(5) In a fifth aspect of the present invention, there is provided a TEM sample preparation method including: placing a thin sample including an observation target therein on a sample holder so that a first side surface of the thin sample, which is closer to the desired observation target than a second side surface of the thin sample is to the observation target, is opposed to a focused ion beam column; setting a processing region, which is to be subjected to etching processing by a focused ion beam, to a region of the first side surface; and performing the etching processing to a portion of the thin sample extending from the first side surface thereof to a front surface thereof by irradiating the processing region with the focused ion beam from the focused ion beam column, thereby forming a thin film portion including the observation target and having a thickness direction substantially parallel to a thickness direction of the thin sample.

What is claimed is:
1. A TEM sample preparation method comprising:
placing a sample on a sample holder so that a first side surface of the sample, which is closer to a desired observation target inside the sample than a second side surface of the sample is to the observation target, is opposed to a focused ion beam column;
setting a processing region, which is to be subjected to etching processing by a focused ion beam so as to form a film portion including the observation target and having a thickness direction substantially parallel to a thickness direction of the sample, to a region of the first side surface that is adjacent to the film portion; and performing etching processing to a portion of the sample extending from the first side surface thereof to a front surface thereof by irradiating the processing region with the focused ion beam from the focused ion beam column, wherein the processing region includes a first irradiation region at the front surface side thereof and a second irradiation region at the film portion side thereof, and wherein an irradiation amount of the focused ion beam is set to be larger in the second irradiation region than in the first irradiation region.

2. A TEM sample preparation method according to claim 1, wherein the irradiation amount of the focused ion beam in the second irradiation region is set to be twice to ten times as large as the irradiation amount of the focused ion beam in the first irradiation region.

3. A TEM sample preparation method according to claim 1, wherein the etching processing includes forming a bottom surface which connects with the front surface and the film portion and is substantially parallel to the first side surface.

4. A TEM sample preparation method comprising:

placing a sample including an observation target therein on a sample holder so that a first side surface of the thin sample, which is closer to the desired observation target than a second side surface of the sample is to the observation target, is opposed to a focused ion beam column;

setting a processing region, which is to be subjected to etching processing by a focused ion beam, to a region of the first side surface; and performing etching processing to a portion of the sample extending from the first side surface thereof to a front surface thereof by irradiating the processing region with the focused ion beam from the focused ion beam column, thereby forming a film portion including the observation target and having a thickness direction substantially parallel to a thickness direction of the sample, wherein the processing region includes a first irradiation region at the front surface side thereof and a second irradiation region at the film portion side thereof, and wherein an irradiation amount of the focused ion beam is set to be larger in the second irradiation region than in the first irradiation region.

5. A TEM sample preparation method comprising:

providing a sample having opposed front and rear surfaces bounded by side surfaces and having inside thereof a desired observation target;

placing the sample on a sample holder so that one side surface of the sample that is closest to the observation target is opposed to a focused ion beam column;

setting a processing region, which is to be subjected to etching processing, to a region of the one side surface of the sample, the processing region having two inner irradiation regions sandwiching therebetween a portion of the sample that has the observation target, and two outer irradiation regions, one extending from the front surface to one of the inner irradiation regions and the other extending from the rear surface to the other of the inner irradiation regions; and performing etching processing of the sample by irradiating the processing region with a focused ion beam from the focused ion beam column to form a TEM sample containing the observation target, the irradiation amount of the focused ion beam being larger when etching processing in the inner irradiation regions than when etching processing in the outer irradiation regions.

6. The TEM sample preparation method according to claim 5; wherein the setting a processing region comprises setting the processing region on a SIM image of the one side surface of the sample.

7. The TEM sample preparation method according to claim 5; wherein the irradiation amount of the focused ion beam when etching processing in the inner irradiation regions is two to ten times larger than the irradiation amount when etching processing in the outer irradiation regions.

8. The TEM sample preparation method according to claim 5; wherein the etching process includes forming a bottom surface which connects the front and rear surfaces to the TEM sample and which is substantially parallel to the one side surface.

9. The TEM sample preparation method according to claim 5; wherein the etching process is performed to form a TEM sample having a thickness of 50 nm or less.

* * * * *